US008735088B2

(12) United States Patent
Durack

(10) Patent No.: US 8,735,088 B2
(45) Date of Patent: May 27, 2014

(54) METHOD TO ANALYZE A SAMPLE FLUID IN A MICROFLUIDIC CYTOMETRY SYSTEM

(75) Inventor: Gary P. Durack, Urbana, IL (US)

(73) Assignees: Sony Corporation, Tokyo (JP); Sony Corporation of America, New York, NY (US)

(*) Notice: Subject to any disclaimer, the term of this patent is extended or adjusted under 35 U.S.C. 154(b) by 788 days.

(21) Appl. No.: 12/830,876

(22) Filed: Jul. 6, 2010

(65) Prior Publication Data
US 2011/0008818 A1 Jan. 13, 2011

Related U.S. Application Data

(60) Provisional application No. 61/223,412, filed on Jul. 7, 2009, provisional application No. 61/223,413, filed on Jul. 7, 2009.

(51) Int. Cl.
C12Q 1/02 (2006.01)
C12Q 1/04 (2006.01)
C12Q 1/10 (2006.01)
B01D 50/00 (2006.01)

(52) U.S. Cl.
USPC .............................. 435/29; 422/72

(58) Field of Classification Search
USPC .............................. 422/72; 435/29
See application file for complete search history.

(56) References Cited

U.S. PATENT DOCUMENTS 3,526,219 A 9/1970 Balamuth
3,814,098 A 6/1974 Deaton
3,861,877 A 1/1975 Matharani et al.
4,256,405 A 3/1981 Fjarlie
4,465,488 A 8/1984 Richmond
4,867,908 A 9/1989 Recktenwald et al.
5,157,465 A 10/1992 Kronberg
5,315,122 A 5/1994 Pinsky et al.
5,466,572 A 11/1995 Sasaki et al.
5,478,722 A 12/1995 Caldwell
5,550,060 A 8/1996 Saunders et al.
5,726,751 A 3/1998 Altendorf et al.
5,793,485 A 8/1998 Gourley
6,245,508 B1 6/2001 Heller et al.
6,268,219 B1 7/2001 McBride et al.
6,280,960 B1 8/2001 Carr
6,632,399 B1 10/2003 Kellogg et al.
6,877,528 B2 4/2005 Gilbert et al.
6,900,021 B1 5/2005 Harrison et al.
7,214,298 B2 5/2007 Spence et al.
7,351,376 B1 4/2008 Quake et al.
2002/0005354 A1 1/2002 Spence et al.
2002/0173033 A1 11/2002 Hammerick et al.
2003/0054558 A1 3/2003 Kurabayashi et al.
2004/0219662 A1 11/2004 Geiger
2004/0224380 A1 11/2004 Chou et al.
2005/0006238 A1 1/2005 Jaffe
2005/0009060 A1 1/2005 Beernink et al.
2005/0105077 A1 5/2005 Padmanabhan et al.
2005/0112541 A1 5/2005 Durack et al.
2005/0260175 A1 11/2005 Hedrick et al.
2006/0011478 A1 1/2006 Fouillet et al.
2006/0024756 A1 2/2006 Tibbe et al.
2006/0134003 A1 6/2006 Georgakoudi et al.
2006/0194264 A1 8/2006 Sheppard et al.
2006/0281143 A1 12/2006 Liu et al.
2007/0095669 A1 5/2007 Lau et al.
2007/0183934 A1 8/2007 Diercks et al.
2007/0190525 A1 8/2007 Gu et al.
2007/0215528 A1* 9/2007 Hayenga et al. ............. 209/576
2007/0240495 A1 10/2007 Hirahara
2007/0263477 A1 11/2007 Sudarsan et al.
2008/0003690 A1 1/2008 Chow
2008/0047836 A1 2/2008 Strand et al.
2008/0072663 A1 3/2008 Keenan et al.
2008/0107386 A1 5/2008 Kudou et al.
2008/0108120 A1* 5/2008 Cho et al. .................... 435/173.7
2008/0176212 A1 7/2008 Spence et al.
2008/0213915 A1 9/2008 Durack et al.
2008/0300148 A1 12/2008 Lee et al.
2009/0027666 A1 1/2009 Godin et al.
2009/0051912 A1 2/2009 Salazar et al.
2009/0053686 A1 2/2009 Ward et al.
2009/0054529 A1 2/2009 Neas et al.
2009/0081688 A1 3/2009 Luo et al.
2009/0195852 A1 8/2009 Bassler et al.

FOREIGN PATENT DOCUMENTS

WO WO 02/40978 A2 5/2002
WO WO 2008/019448 A1 2/2008

OTHER PUBLICATIONS

Huh et al. 2005. Microfluidics for flow cytometric analysis of cells and particles. Physiol. Meas., vol. 26, pp. R73-R98.*
Madou et al. 1988. The LabCDTM: A Centrifuge-Based Microfluidic Platform for Diagnostics. Proc. SPIE 3259, Systems and Technologies for Clinical Diagnostics and Drug Discovery, Feb. 12, 1988, pp. 80-93.*
GE Healthcare. 2007. Ficoll-Paque Intended Use for in vitro isolation of lymphocytes. Instructions 71-7167-00 AG, Feb. 2007 pp. 1-16).*
International Search Report and Written Opinion issued in PCT/US2010/040923, mailed Aug. 30, 2010.
International Search Report and Written Opinion Issued in PCT/US2010/041058, mailed Sep. 7, 2010.
International Search Report and Written Opinion issued in PCT/US2010/041062, mailed Aug. 20, 2010.
International Search Report and Written Opinion issued in PCT/US2010/041067, mailed Sep. 22, 2010.

(Continued)

Primary Examiner — Jon P Weber
Assistant Examiner — Kailash C Srivastava
(74) Attorney, Agent, or Firm — Ice Miller LLP

(57) ABSTRACT

The present disclosure relates to microfluidic devices adapted for post-centrifugation use with selective sample extraction, and methods for their use. Certain embodiments make use of a dye-selective sample extraction. Other embodiments make use of a geographically-selective sample extraction. Other embodiments are also disclosed.

11 Claims, 5 Drawing Sheets

(56) References Cited

OTHER PUBLICATIONS

International Search Report and Written Opinion issued in PCT/US2010/041094, mailed Sep. 2, 2010.
Nederlof et al. Multiple Fluorescence in situ hybridization; Cytometry, 1990, vol. 11, Iss. 1, pp. 126-131.
International Search Report and Written Opinion issued in PCT/US2010/041087, mailed Oct. 26, 2010.
International Search Report and Written Opinion Issued in PCT/US2010/041090, mailed Oct. 13, 2010.
Kang et al. Technical Paper on Microfluidic Devices Cell Separation Technology, Paper, Dec. 2005.
Tsutsui et al. Cell Separation by Non-Inertial Force Fields in Microfluidic Systems; Manuscript, Jan. 1, 2009.

* cited by examiner

US 8,735,088 B2

METHOD TO ANALYZE A SAMPLE FLUID IN A MICROFLUIDIC CYTOMETRY SYSTEM

CROSS-REFERENCE TO RELATED APPLICATIONS

The present application claims the benefit of U.S. Provisional Patent Application No. 61/223,412, which was filed Jul. 7, 2009. The present application also claims the benefit of U.S. Provisional Application No. 61/223,413, filed Jul. 7, 2009. Both of these applications are incorporated herein by reference in their entireties

TECHNICAL FIELD OF THE INVENTION

The present disclosure relates generally to microfluidic cytometry systems and, more particularly, to a microfluidic device adapted for post-centrifugation use with selective sample extraction and methods for its use.

BACKGROUND OF THE INVENTION

Flow cytometry-based cell sorting was first introduced to the research community more than 20 years ago. It is a technology that has been widely applied in many areas of life science research, serving as a critical tool for those working in fields such as genetics, immunology, molecular biology and environmental science. Unlike bulk cell separation techniques such as immuno-panning or magnetic column separation, flow cytometry-based cell sorting instruments measure, classify and then sort individual cells or particles serially at rates of several thousand cells per second or higher. This rapid "one-by-one" processing of single cells has made flow cytometry a unique and valuable tool for extracting highly pure sub-populations of cells from otherwise heterogeneous cell suspensions.

Cells targeted for sorting are usually labeled in some manner with a fluorescent material. The fluorescent probes bound to a cell emit fluorescent light as the cell passes through a tightly focused, high intensity, light beam (typically a laser beam). A computer records emission intensities for each cell. These data are then used to classify each cell for specific sorting operations. Flow cytometry-based cell sorting has been successfully applied to hundreds of cell types, cell constituents and microorganisms, as well as many types of inorganic particles of comparable size.

Flow cytometers are also applied widely for rapidly analyzing heterogeneous cell suspensions to identify constituent sub-populations. Examples of the many applications where flow cytometry cell sorting is finding use include isolation of rare populations of immune system cells for AIDS research, isolation of genetically atypical cells for cancer research, isolation of specific chromosomes for genetic studies, and isolation of various species of microorganisms for environmental studies. For example, fluorescently labeled monoclonal antibodies are often used as "markers" to identify immune cells such as T lymphocytes and B lymphocytes, clinical laboratories routinely use this technology to count the number of "CD4 positive" T cells in HIV infected patients, and they also use this technology to identify cells associated with a variety of leukemia and lymphoma cancers.

Recently, two areas of interest are moving cell sorting towards clinical, patient care applications, rather than strictly research applications. First is the move away from chemical pharmaceutical development to the development of biopharmaceuticals. For example, the majority of novel cancer therapies are now biologics containing proteins or peptides. These include a class of antibody-based cancer therapeutics. Cytometry-based cell sorters can play a vital role in the identification, development, purification and, ultimately, production of these products.

There is also a move toward the use of cell replacement therapy for patient care. Much of the current interest in stem cells revolves around a new area of medicine often referred to as regenerative therapy or regenerative medicine. These therapies may often require that large numbers of relatively rare cells be isolated from sample patient tissue. For example, adult stem cells may be isolated from bone marrow or adipose tissue and ultimately used as part of a re-infusion back into the patient from whom they were removed. Cytometry lends itself very well to such therapies.

There are two basic types of cell sorters in wide use today. They are the "droplet cell sorter" and the "fluid switching cell sorter." The droplet cell sorter utilizes micro-droplets as containers to transport selected cells to a collection vessel. The micro-droplets are formed by coupling ultrasonic energy to a jetting stream. Droplets containing cells selected for sorting are then electrostatically steered to the desired location. This is a very efficient process, allowing as many as 90,000 cells per second to be sorted from a single stream, limited primarily by the frequency of droplet generation and the time required for illumination.

A detailed description of a prior art flow cytometry system is given in United States Published Patent Application No. US 2005/0112541 A1 to Durack et al.

Droplet cell sorters, however, are not particularly biosafe. Aerosols generated as part of the droplet formation process can carry biohazardous materials. Because of this, biosafe droplet cell sorters have been developed that are contained within a biosafety cabinet so that they may operate within an essentially closed environment. Unfortunately, this type of system does not lend itself to the sterility and operator protection required for routine sorting of patient samples in a clinical environment.

The second type of flow cytometry-based cell sorter is the fluid switching cell sorter. Most fluid switching cell sorters utilize a piezoelectric device to drive a mechanical system which diverts a segment of the flowing sample stream into a collection vessel. Compared to droplet cell sorters, fluid switching cell sorters have a lower maximum cell sorting rate due to the cycle time of the mechanical system used to divert the sample stream. This cycle time, the time between initial sample diversion and when stable non-sorted flow is restored, is typically significantly greater than the period of a droplet generator on a droplet cell sorter. This longer cycle time limits fluid switching cell sorters to processing rates of several hundred cells per second. For the same reason, the stream segment switched by a fluid cell sorter is usually at least ten times the volume of a single micro-drop from a droplet generator. This results in a correspondingly lower concentration of cells in the fluid switching sorter's collection vessel as compared to a droplet sorter's collection vessel.

Newer generation microfluidics technologies offer great promise for improving the efficiency of fluid switching devices and providing cell sorting capability on a chip similar in concept to an electronic integrated circuit. Many microfluidic systems have been demonstrated that can successfully sort cells from heterogeneous cell populations. They have the advantages of being completely self-contained, easy to sterilize, and can be manufactured on sufficient scales (with the resulting manufacturing efficiencies) to be considered a disposable part.

A generic microfluidic device is illustrated in FIG. 1 and indicated generally at 10. The microfluidic device 10 comprises a substrate 12 having a fluid flow channel 14 formed therein by any convenient process as is known in the art. The substrate 12 may be formed from glass, plastic or any other convenient material, and may be substantially transparent or substantially transparent in a portion thereof. In certain embodiments, the substrate 12 is injection molded. In certain embodiments, the substrate 12 comprises industrial plastic such as a Cyclo Olefin Polymer (COP) material, or other plastic. As a result, the substrate 12 is transparent such that a cytometry optics module can analyze the sample fluid stream as described further below. In one embodiment, the microfluidic device 10 is disposable.

The substrate 12 further has three ports 16, 18 and 20 coupled thereto. Port 16 is an inlet port for a sheath fluid. Port 16 has a central axial passage that is in fluid communication with a fluid flow channel 22 that joins fluid flow channel 14 such that sheath fluid entering port 16 from an external supply (not shown) will enter fluid flow channel 22 and then flow into fluid flow channel 14. The sheath fluid supply may be attached to the port 16 by any convenient coupling mechanism as is known to those skilled in the art. In one embodiment, the sheath fluid comprises a buffer or buffered solution. For example, the sheath fluid comprises 0.96% Dulbecco's phosphate buffered saline (w/v), 0.1% BSA (w/v), in water at a pH of about 7.0.

Port 18 also has a central axial passage that is in fluid communication with a fluid flow channel 14 through a sample injection tube 24. Sample injection tube 24 is positioned to be coaxial with the longitudinal axis of the fluid flow channel 14. Injection of a liquid sample of cells into port 18 while sheath fluid is being injected into port 16 will therefore result in the cells flowing through fluid flow channel 14 surrounded by the sheath fluid. The dimensions and configuration of the fluid flow channels 14 and 22, as well as the sample injection tube 24 are chosen so that the sheath/sample fluid will exhibit laminar flow as it travels through the device 10, as is known in the art. Port 20 is coupled to the terminal end of the fluid flow channel 14 so that the sheath/sample fluid may be removed from the microfluidic device 10.

While the sheath/sample fluid is flowing through the fluid flow channel 14, it may be analyzed using cytometry techniques by shining an illumination source through the substrate 12 and into the fluid flow channel 14 at some point between the sample injection tube 24 and the outlet port 20. Additionally, the microfluidic device 10 could be modified to provide for a cell sorting operation, as is known in the art.

Although basic microfluidic devices similar to that described hereinabove have been demonstrated to work well, there is a need in the prior art for improvements to cytometry systems employing microfluidic devices. The present invention is directed to meeting this need.

SUMMARY OF THE DISCLOSURE

The present disclosure relates to microfluidic devices adapted for post-centrifugation use with selective sample extraction, and methods for their use. Certain embodiments make use of a dye-selective sample extraction. Other embodiments make use of a geographically-selective sample extraction.

In certain embodiments, a method of analyzing a sample fluid in a microfluidic cytometry system is disclosed, the method comprising the steps of a) supplying a sample to a sample well in a microfluidic device; b) centrifuging the microfluidic device to create a first sample layer and a second sample layer within said sample well; c) extracting first fluid from said first sample layer; and d) analyzing said extracted first fluid using cytometry while said extracted first fluid is in the microfluidic device.

In other embodiments, a microfluidic device is disclosed, comprising a sample well having a sample input port for receiving a sample into the microfluidic device, said sample well having a first end and a second end, and a sample output port in fluid communication with said sample well, said sample output port located between said first end and said second end, wherein sample may be withdrawn through said sample output port to form a withdrawn sample and said withdrawn sample is not withdrawn at said first end or at said second end.

In further embodiments, a microfluidic device is disclosed, comprising a sample well having a sample input port for receiving a sample into the microfluidic device, said sample well having a first end and a second end, a first sample output port in fluid communication with said sample well, said first sample output port located between said first end and said second end, and a second sample output port in fluid communication with said sample well, said second sample output port located between said first sample output port and said second end, wherein sample may be withdrawn through said first sample output port to form a first withdrawn sample and said first withdrawn sample is not withdrawn at said first end or at said second end, and wherein sample may be withdrawn through said second sample output port to form a second withdrawn sample and said second withdrawn sample is not withdrawn at said first end or at said second end.

Other embodiments are also disclosed.

DESCRIPTION OF THE ILLUSTRATED EMBODIMENTS

Figure 1:
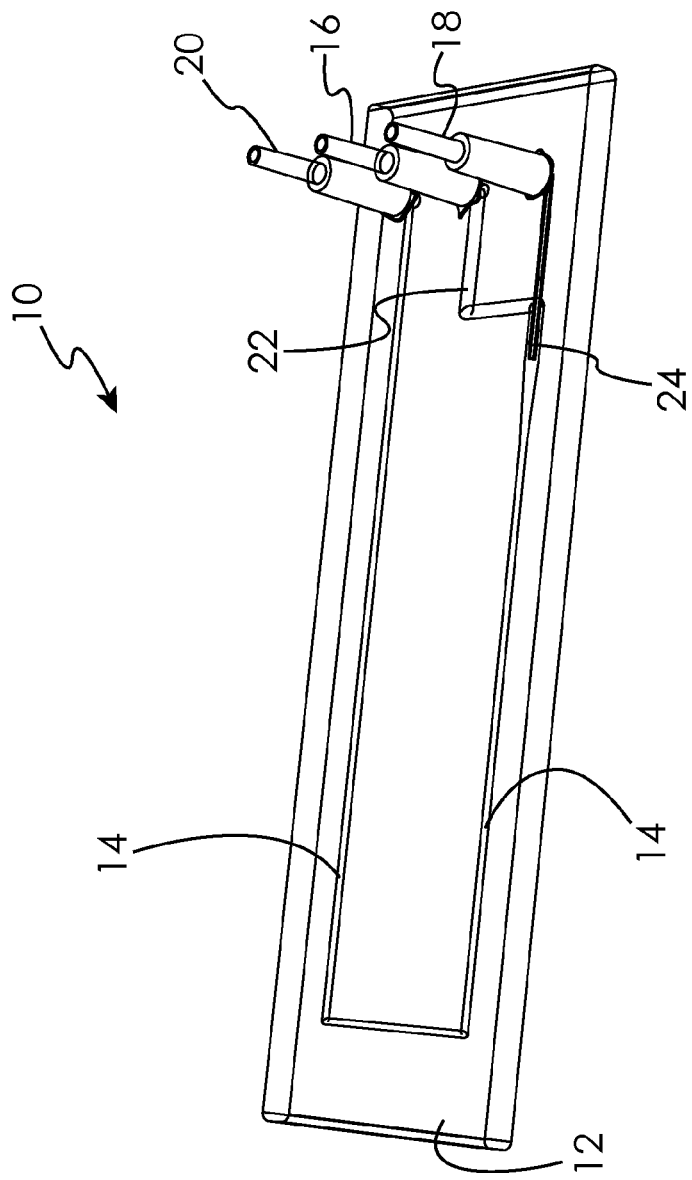
FIG. 1 is a perspective view of a prior art microfluidic device.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein are contemplated as would normally occur to one skilled in the art to which the disclosure relates.

The present disclosure is generally directed to systems for the separation and/or analysis of a biological sample on a microfluidic device using cytometry (such as flow cytometry or image cytometry). To increase the efficiency of cytometry operations, it is desirable to start with a sample containing mostly those types of cells that are desired to be individually studied or isolated. One method known in the art is to subject the sample to centrifugation prior to cytometry analysis. After centrifugation, the sample components will be separated into layers. Due to factors such as mass, density and specific gravity, the desired component, or cell population, can then be more easily extracted. This process is common laboratory practice and many common sample containers and centrifuge devices are commercially available for this purpose. However, this procedure introduces the possibility that the sample layers will become remixed during the transfer from the initial collection vessel to the microfluidic device. By adapting the microfluidic device itself to be suitable for containing the sample during the centrifugation process, the possibility of layer mixing after centrifugation and prior to analysis by the cytometer is reduced. This also eliminates the need for multiple containers and reduces the possibility of outside contaminates being introduced into the sample (or potentially harmful sample components being released into the outside environment). Since the microfluidic device can be manufactured to be sterile (e.g. exposed to gamma irradiation), the entire process of centrifugation, cytometry measurement, and sorted fraction collection can be conducted in a closed, sterile environment. Most importantly, the centrifugation process and transfer of material among containers can introduce loss of 10% or more of the cells. When low cell numbers are involved this loss is intolerable, in fact it is impossible to apply even microcentrifugation in many cases where sample volume is low.

Dye-Selective Sample Extraction

Figure 2:
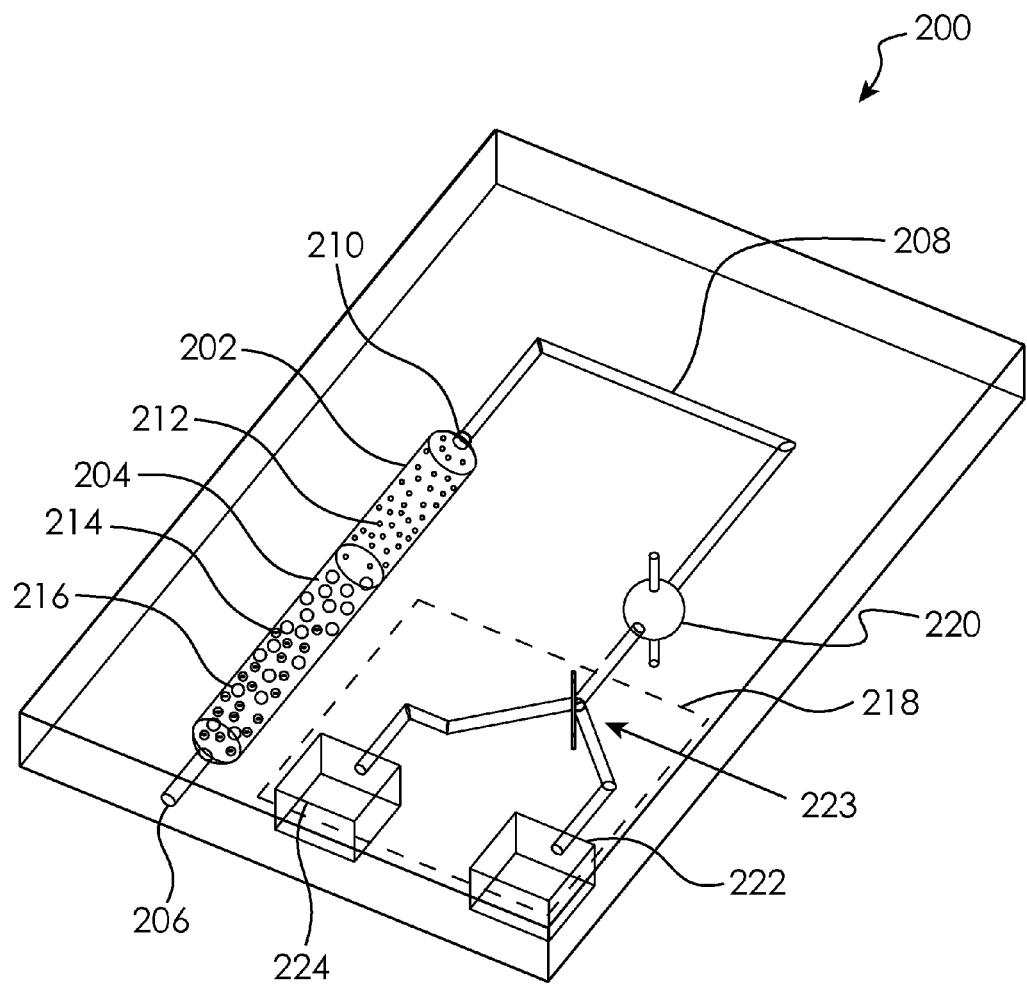
FIG. 2 is a schematic front view of a microfluidic device according to a first embodiment of the present disclosure.

In one embodiment, FIG. 2 illustrates a device 200 which is configured to achieve the separation of biological components contained within a sample. The device 200 includes a sample well 202 for receiving a sample 204 from an external source (not shown) via port 206. In certain embodiments, the sample well 202 is elongated to facilitate gradient separation of the sample components when the device 200 is placed in a centrifuge. Various chemical additives known in the art and commonly used to facilitate the process of separation based on the density of sample constituents, such as Ficoll-Hypaque to name just one non-limiting example, may be added to the sample 204 to increase the separation effect. In certain embodiments, such chemical additives may be added to the sample well 202 during manufacturing, eliminating the need for the user to add them during the sampling process. In addition, in certain embodiments a dye may be added to the Ficoll-Hypaque to provide a color distinction between the layers as described hereinbelow.

As will be appreciated by those skilled in the art, the microfluidic device may be subjected to the forces of centrifugation in either direction along the longitudinal axis of the sample well 202. With the Ficoll-Hypaque method, the cells are layered on to the Ficoll-Hypaque solution, so that the cells are "on top" relative to the force of centrifugation. In other embodiments and other additives, the entire situation might be inverted. By using the microfluidic device as the container for the sample before analysis, during centrifugation, during analysis and/or after sorting, the user may move the small sample from a centrifuge in one part of the laboratory to a cytometer somewhere else, and then after analysis the sample may be transported to a third location, all in a sterile environment.

Channel 208 is connected via port 210 at one end of sample well 202 to retrieve the desired sample component after centrifugation. As one non-limiting example, human blood may be injected into the sample well 202 after which the device 200 is subjected to centrifugation to separate the mononuclear cells 212, i.e. lymphocytes and monocytes, from the larger granulocytic cells 214 and red blood cells 216. After centrifugation, the port 210 may be opened to allow the sample 204 to flow through channel 208 to a cytometry analysis section 218 within device 200 for further cytometric analysis and/or separation. For example, the cytometry analysis section 218 may image the cells in the flow channel prior to switching element 223 and then divert a subset of the mononuclear cells previously isolated, by identifying them using image or common fluorescence-based methods, and then exercising appropriate control of a switching element 223, into an extraction well 222 and undesirable cells into a waste well 224. In certain embodiments, the wells 222 and 224 communicate with ports (not shown) to allow extraction of their contents from the microfluidic device 200. The specific analysis and/or sorting performed in analysis section 218 is not critical to the present disclosure and may be performed in a variety of different manners in different embodiments.

In certain embodiments, the sorting performed by the cytometry analysis section 218 is greater than a binary sort. In other embodiments, the sorting performed by the cytometry analysis section 218 is greater than a tertiary sort. In other embodiments, the sorting performed by the cytometry analysis section 218 is greater than a quartnery sort. In executing the sort, certain embodiments comprise at least five channels. Other embodiments comprise at least ten channels. Other embodiments comprise at least 100 channels. Other embodiments comprise at least 256 channels.

The flow through channel 208 may be initiated by capillary action or other microfluidic flow means known in the art. Such methods may require that additional channels or features (not shown) be included in the microfluidic device. In one embodiment, sample cells are added to the sample well 202 first and then the Ficoll-Hypaque solution is added. The microfluidic device is then subjected to centrifugation with the applied force being toward the port 206. As the sample flows through the channel 208, the lighter mononuclear cells 212 will be drawn off first. The cytometry analysis and sorting section 218 is programmed to close the port 210 or, in alternative embodiments, a valve 220, upon the detection by analysis section 218 of the particular dye contained within the Ficoll-Hypaque solution. In this case the dye will be in the same layer as the plasma-Ficoll interface which is just below the layer of lymphocytes. The granulocytic cells 214 and red blood cells 216 would be held below the plasma-Ficall interface layer and, therefore, the dye. This allows the full amount of mononuclear cells 212 contained in the sample 204 to be extracted while still rejecting the undesired components within the gradient separation. In a second example, necrotic cells can easily be separated without any chemical additives due to their higher density. In addition to blood, the present disclosure contemplates that other types of biological or chemical samples may be analyzed in this manner, it being understood that the present disclosure is useful with any sample that can be separated by centrifugation.

When dye is added to the sample solution, it must be done in such a way that the dye ends up in the correct layer after centrifugation. In certain embodiments, the dye may be designed to have the correct density to achieve this. In other embodiments, the dye can be bonded at the molecular level with the Ficall-Hypaque (or other chemical additive) in a manner that does not negatively impact the specific gravity of the Ficoll-Hypaque.

Figure 3:
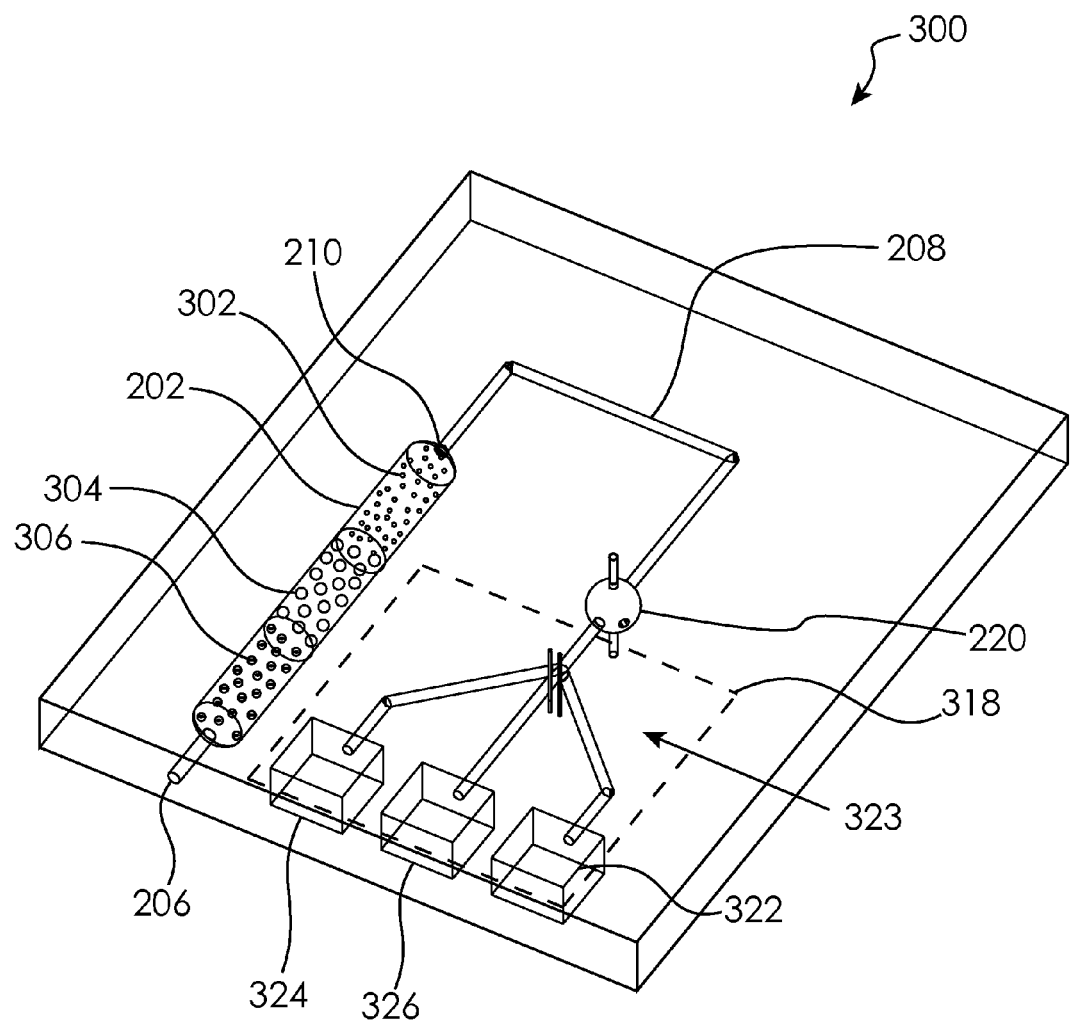
FIG. 3 is a schematic front view of a microfluidic device according to a second embodiment of the present disclosure.

In other embodiments, various density gradient chemicals, each with their own specific gravity and/or dye color, can be used to detect and extract individual components from a sample. For example, as shown in FIG. 3, the cytometry analysis section 318 may be configured to divert sorted cells or particles (such as viral particles) from a first sample component into a first extraction well 322 until the detection of a first colored dye corresponding to the density gradient chemical layer (which holds a second sample component 304). The device 300 is similar to the device 200, and like reference designators are used to designate like components. After centrifugation, the cytometry analysis section 318 will adjust the analysis parameters to account for the new type of cells being analyzed and divert sorted cells into a second extraction well 326. Upon the detection of a second colored dye solution (which holds a third sample component 306), the cytometry analysis section 318 will then adjust the analysis parameters to account for the new type of cells being analyzed and divert all remaining cells into the waste well 324 and/or close valve 220 to cease sample flow. In certain embodiments, the wells 322, 324 and 326 communicate with ports (not shown) to allow extraction of their contents from the microfluidic device 300. The specific analysis and/or sorting performed in analysis section 318 is not critical to the present disclosure and may be performed in a variety of different manners in different embodiments.

In certain embodiments, the sorting performed by the cytometry analysis section 318 is greater than a binary sort. In other embodiments, the sorting performed by the cytometry analysis section 318 is greater than a tertiary sort. In other embodiments, the sorting performed by the cytometry analysis section 318 is greater than a quartnery sort. In executing the sort, certain embodiments comprise at least five channels. Other embodiments comprise at least ten channels. Other embodiments comprise at least 100 channels. Other embodiments comprise at least 256 channels.

In certain embodiments, the microfluidic devices comprise two or more pieces. The two pieces are coupled together using any desirable means such as, by way of non-limiting example, a thermal bonding process, an ultrasonic welding process or an adhesive process. In one embodiment the two pieces are halves. In another embodiment, the two pieces are divided asymmetrically in the plane, e.g. a planar cover and a piece containing channels. In still other embodiments, multiple pieces are assembled. Other ways of coupling the two pieces will be readily apparent to one skilled in the art depending upon the material used to fabricate the microfluidic device.

Geographically-Selective Sample Extraction

Figure 4:
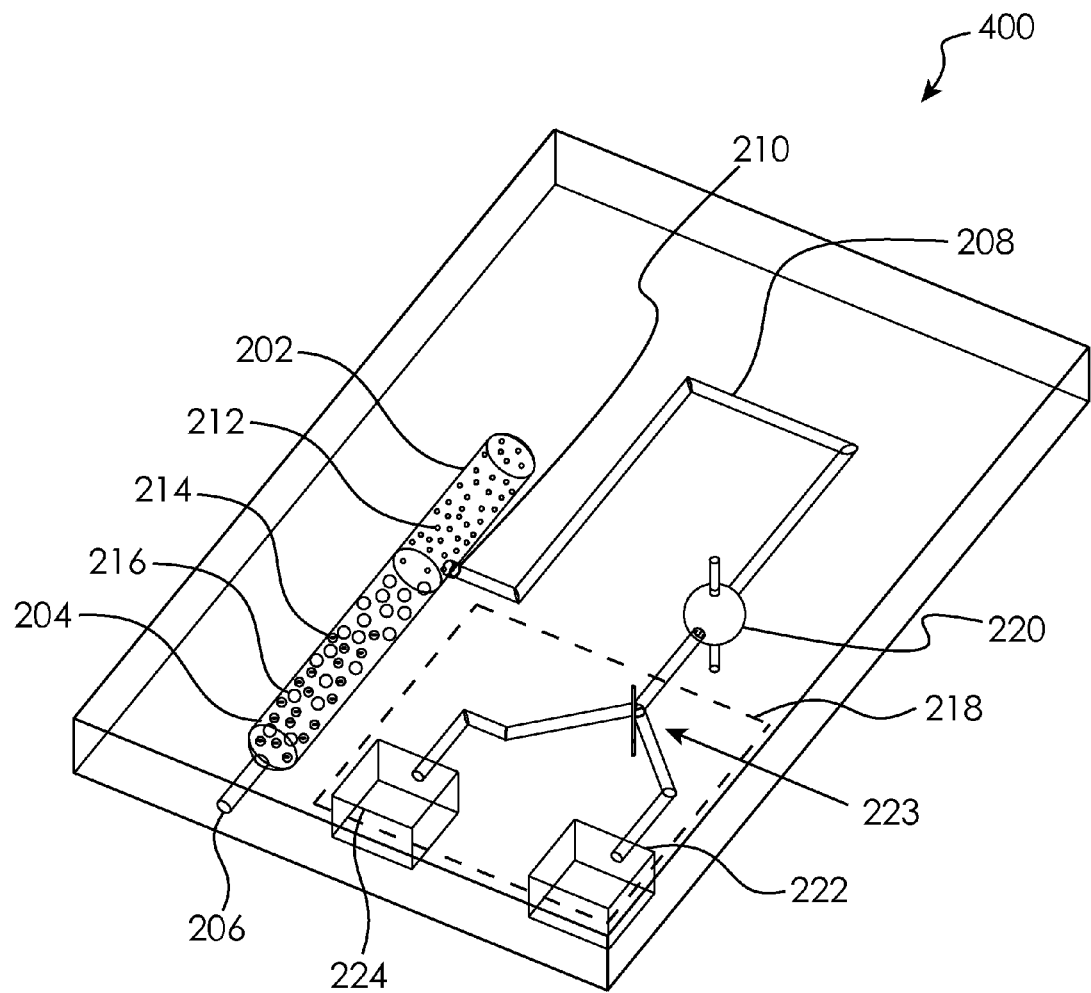
FIG. 4 is a schematic front view of a microfluidic device according to a third embodiment of the present disclosure.

FIG. 4 illustrates another embodiment, in which a device 400 which is configured to achieve the separation of biological components contained within a sample. The device 400 is similar to the device 200, and like reference designators are used to designate like components. The device 400 includes a sample well 202 for receiving a sample 204 from an external source (not shown) via port 206. The sample well 202 is elongated to facilitate gradient separation of the sample components when the device 400 is placed in a centrifuge. Various chemical additives known in the art, such as Ficoll-Hypaque, may be added to the sample 204 to increase the separation effect as described hereinabove. In certain embodiments, such chemical additives may be added to the sample well 202 during manufacturing, eliminating the need for the user to add them during the sampling process.

Channel 208 is connected via port 210 at a specific location along the length of sample well 202 to retrieve the desired sample component after centrifugation. The exact location of the port 210 is determined by the nature of the sample being processed and the component desired to be extracted, such that the placement of the port 210 is designed to be in close physical proximity to the position of the component desired to be extracted after centrifugation. This ensures that a maximum volume of the desired sample component may be extracted from the sample well 202. It will be appreciated, therefore, that the placement of the port 210 in the device 400 is made strategically to more precisely align with the location of the desired sample component than the device 200 illustrated in FIG. 2.

As one non-limiting example, human blood may be injected into the sample well 202 after which the device 400 is subjected to centrifugation to separate the mononuclear cells 212, i.e. lymphocytes and monocytes, from the larger granulocytic cells 214 and red blood cells 216. After centrifugation, the port 210 may be opened to allow the sample 204 to flow through channel 208 to a cytometry analysis section 218 within device 400 for further cytometric analysis and/or separation. For example, the cytometry analysis section 218 may divert sorted desirable cells, by appropriate control of the switching device 223, into an extraction well 222 and undesirable cells into a waste well 224. In certain embodiments, undesirable cells may also be expelled from the device 400 through a waste port (not shown). The specific analysis and/or sorting performed in analysis section 218 is not critical to the present disclosure.

The flow through channel 208 may be initiated by capillary action or other microfluidic pumping means known in the art. As the sample flows through the channel 208, the lighter mononuclear cells 212 will be drawn off first due to their proximity to the port 210. In certain embodiments, multiple channels 208 and multiple ports 210 may be connected along the sample well 202 within the region of the desired sample component (such as mononuclear cells 212) to facilitate more complete extraction of the desired sample component. The cytometry analysis section 218 is programmed to close the port 210 or, in alternative embodiments, a valve 220, after a certain amount of sample fluid or cells has been extracted. This amount depends on the volume of the sample 204, the nature of the sample being processed, and the expected volume of the desired component layer.

For simplicity and ease of illustration, the presently illustrated embodiments show single channels extending between the components, areas or sections of the illustrated devices. However, it should be appreciated that the single channels may be representative of multiple cytometry channels and a variety of possible configurations of channels as would occur to one skilled in the art.

Figure 5:
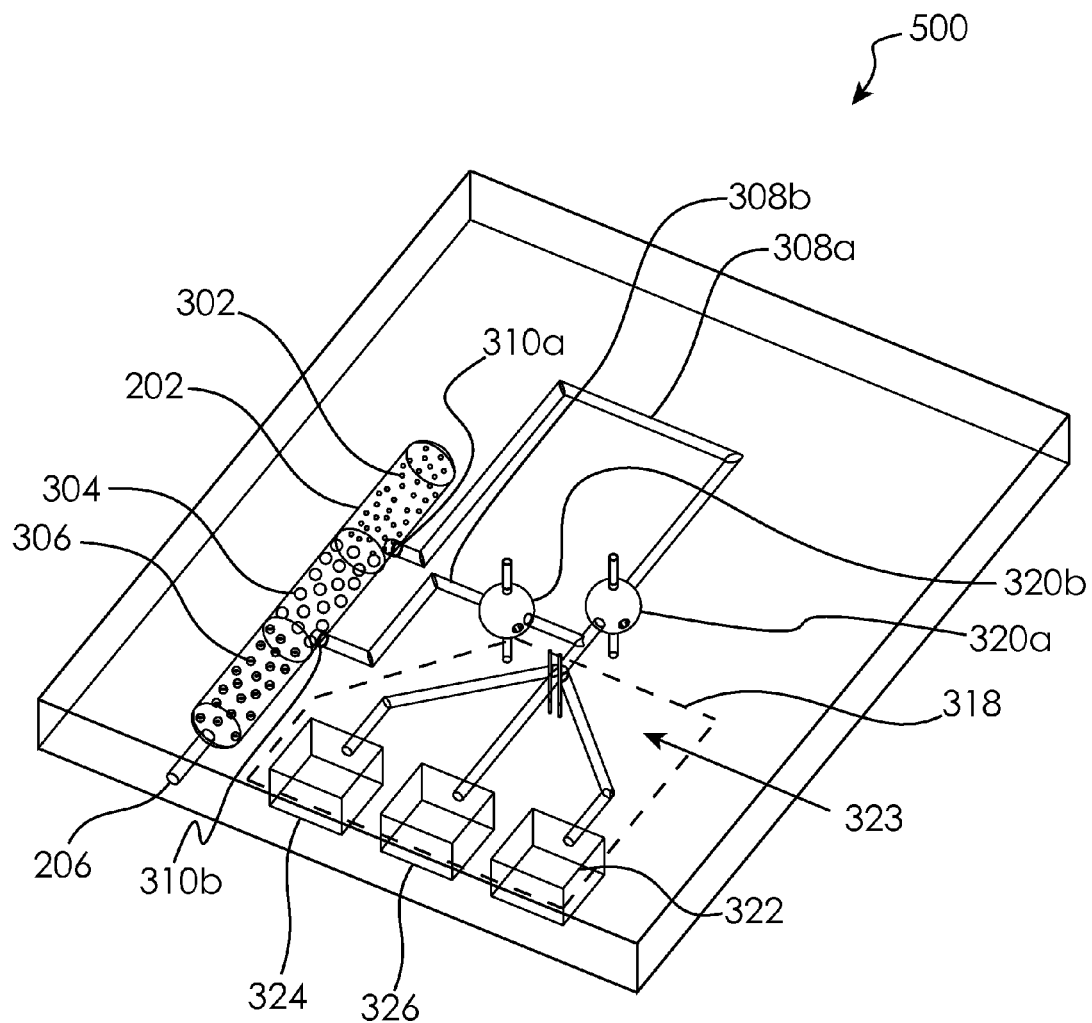
FIG. 5 is a schematic front view of a microfluidic device according to a fourth embodiment of the present disclosure.

In other embodiments, multiple channels can be used to extract multiple components from a sample. The addition of two or more types of Ficoll-Hypaque (or other appropriate additive) can also be used to create additional layers in the centrifuged sample. For example, as shown in FIG. 5, a device 500 is provided into which an analysis sample 202 may be loaded through port 206. By the use of appropriate additives as discussed herein, the analysis sample may, for example, be divided into three layers 302, 304 and 306 post-centrifugation. The device 500 is adapted to selectively extract sample from the layers 302 and 304 by positioning ports 310a and 310b, respectively, in alignment with the layers 302 and 304. Port 310a and or valve 320a may be opened to allow sample 302 to flow through the channel 308a. A cytometry analysis section 318 may be configured to divert sorted cells from the first sample component 302 into a first extraction well 322 by control of valve 323. Similarly, undesired cells from the first sample component 302 may be diverted to waste well 324 by appropriate control of the valve 323. Once the cytometry section 318 determines that analysis of the first sample component 302 is complete, the cytometry analysis section 318 is programmed to close the port 310a or, in alternative embodiments, a valve 320a.

The cytometry analysis section 318 will then adjust the analysis parameters to account for the new type of cells being analyzed, open port 310b, allowing fluid from the second sample component 304 to flow to the cytometry analysis section 318, and divert sorted cells into a second extraction well 326 by appropriate control of valve 323. Once the cytometry section 318 determines that analysis of the second sample component 304 is complete, the cytometry analysis section 318 is programmed to close the port 310*b* or, in alternative embodiments, a valve 320*b*.

It will be appreciated that by proper location of the ports 310*a* and 310*b*, the device 500 may take advantage of the multiple layers of sample post-centrifugation. Analysis and sorting of the sample components is made easier by separating the sample components into layers using centrifugation, and then extracting sample components in a purer form by means of strategic location of the extraction ports 310. It will be appreciated by those skilled in the art that any number of extraction ports may be utilized to more precisely extract post-centrifugation samples from the analysis sample.

While the disclosure has been illustrated and described in detail in the drawings and foregoing description, the same is to be considered as illustrative and not restrictive in character, it being understood that only the preferred embodiments have been shown and described and that all changes and modifications that come within the spirit of the disclosure are desired to be protected.

What is claimed:

1. A method of analyzing a sample fluid in a microfluidic cytometry system, the method comprising the steps of:
    a) supplying a sample to a sample well in a microfluidic device;
    b) centrifuging the microfluidic device to create a first sample layer and a second sample layer within said sample well;
    c) extracting first fluid from said first sample layer; and
    d) analyzing said extracted first fluid using cytometry while said extracted first fluid is in the microfluidic device.

2. The method of claim 1, further comprising the steps of:
    e) sorting a first portion of said extracted first fluid into a first well based upon results obtained in step (d); and
    f) sorting a second portion of said extracted first fluid into a second well based upon results obtained in step (d).

3. The method of claim 2, wherein said sorting at steps (e) and (f) is selected from the group consisting of: greater than a binary sort, greater than a tertiary sort, greater than a quaternary sort.

4. The method of claim 2, wherein said sorting at steps (e) and (f) employs a predetermined number of microfluidic channels, said predetermined number selected from the group consisting of: at least five channels, at least ten channels, at least 100 channels, and at least 256 channels.

5. The method of claim 2, further comprising the steps of:
    g) extracting second fluid from said second sample layer; and
    h) analyzing said extracted second fluid using cytometry while said extracted second fluid is in the microfluidic device.

6. The method of claim 5, further comprising the step of:
    i) sorting a third portion of said extracted second fluid into a third well based upon results obtained in step (h).

7. The method of claim 5, wherein:
said extracted first fluid is extracted from said sample well at a first location; and
said extracted second fluid is extracted from said sample well at a second location, said second location being different than said first location.

8. The method of claim 1, further comprising the step of:
adding a chemical additive to said sample well prior to performing step (a).

9. The method of claim 1, further comprising the step of:
adding Ficoll-Hypaque to said sample well prior to performing step (a).

10. The method of claim 1, further comprising the step of:
adding a dye to said sample well prior to performing step (a).

11. The method of claim 1, wherein step (a) further comprises supplying a sample of human blood to a sample well on a microfluidic device.

* * * * *